(12) United States Patent
Yousef et al.

(10) Patent No.: US 12,163,116 B2
(45) Date of Patent: Dec. 10, 2024

(54) AUTOMATED BIOREACTOR WITH FOAM COLLECTOR

(71) Applicant: OHIO STATE INNOVATION FOUNDATION, Columbus, OH (US)

(72) Inventors: Ahmed Yousef, Dublin, OH (US); David Kasler, Ashville, OH (US); Emily Campbell, New Albany, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 1002 days.

(21) Appl. No.: 16/999,193

(22) Filed: Aug. 21, 2020

(65) Prior Publication Data

US 2020/0377840 A1 Dec. 3, 2020

Related U.S. Application Data

(63) Continuation-in-part of application No. PCT/US2019/019184, filed on Feb. 22, 2019.
(Continued)

(51) Int. Cl.
*C12M 1/26* (2006.01)
*C07K 14/195* (2006.01)
(Continued)

(52) U.S. Cl.
CPC ........... *C12M 33/00* (2013.01); *C07K 14/195* (2013.01); *C12M 41/12* (2013.01); *C12M 41/48* (2013.01); *C12P 21/00* (2013.01)

(58) Field of Classification Search
CPC ...... C12M 33/00; C12M 41/02; C12M 41/12; C12M 41/48; C12P 21/02; C12P 21/00; C07K 14/195
See application file for complete search history.

(56) References Cited

U.S. PATENT DOCUMENTS

| 3,445,342 A | 5/1969 | Freedman |
| 4,211,645 A | 7/1980 | Zajic et al. |
| (Continued) | | |

OTHER PUBLICATIONS

Grau, A. et al., Aggregational Behavior of Aqueous Dispersions of the Antifungal Lipopeptide iturin A, Peptides 22, 2001.
(Continued)

*Primary Examiner* — Jana A Hines
(74) *Attorney, Agent, or Firm* — Standley Law Group LLP; Jeffrey S. Standley; Kenny W. Pung

(57) ABSTRACT

An apparatus produces a target metabolite in a bioreaction. The apparatus has a reactor vessel that contains a bulk liquor in which the bioreaction is conducted, with a headspace provided above the bulk liquor. In some instances, the target metabolite is favorably partitioned into a foam formed at an interface of the bulk liquor and the headspace. A foam collector is arranged to receive this foam from the bioreactor and break it into a condensed foam liquid, from which the target metabolite may be isolated and purified. In one exemplary application, paenibacillin is produced by fermentation of a medium by *Paenibacillus polymyxa* OSY-DF, and is preferentially concentrated in the foam. In another exemplary application, fermentation of a medium by *Bacillus velezensis* GF610 produces amyloliquecidin GF610 is which is preferentially concentrated in the foam.

16 Claims, 8 Drawing Sheets

Related U.S. Application Data

(60) Provisional application No. 62/633,937, filed on Feb. 22, 2018.

(51) Int. Cl.
*C12M 1/34* (2006.01)
*C12M 1/36* (2006.01)
*C12P 21/00* (2006.01)

(56) References Cited

U.S. PATENT DOCUMENTS

| | | | |
|---|---|---|---|
| 4,654,305 A | | 3/1987 | Barnett et al. |
| 4,883,759 A | * | 11/1989 | Hopkins ................ C12M 41/24 435/173.7 |
| 6,673,599 B2 | | 1/2004 | Rietschel et al. |
| 2001/0051371 A1 | * | 12/2001 | Kiplinger ............... C12M 29/14 435/262 |

OTHER PUBLICATIONS

Phae, C. et al., Investigation of Optimal Conditions for Foam Separation of Iturin, an Antifungal Petptide Produced by Bacillus subtilis, Journal of Fermentation and Bioengineering, 1991, pp. 118-121, vol. 71.

* cited by examiner

AUTOMATED BIOREACTOR WITH FOAM COLLECTOR

CROSS-REFERENCE TO RELATED APPLICATIONS

This application is a by-pass continuation in-part of application PCT/US2019/019184, filed 22 Feb. 2019, which is in turn a non-provisional of U.S. provisional patent application 62/633,937, filed on 22 Feb. 2018. A priority claim is made to each application and each is incorporated by reference as if fully recited herein.

TECHNICAL FIELD

The disclosed embodiments of the present invention relate to a reactor system, especially one that is adapted for conducting fermentation reactions, especially aerobic industrial fermentations or bioreactions that would be expected to result in generation of foam, which is collected.

BACKGROUND

As used herein, the term "bioreaction" refers to biochemical transformations enabled by enzymes, organisms, tissues, or other biological agents. Based on the need for oxygen, bioreactions can be aerobic or anaerobic. A bioreactor is a device where bioreactions occur. The term "fermentation" can be used in a biological sense to refer to metabolic bioreactions in which an organism uses a carbohydrate to produce energy anaerobically, or in an industrial sense to describe all types of bioreactions, not only metabolic fermentations. A "fermentor" is a device or vessel used to complete fermentations, the work of fermentation being achieved by a "fermenter" organism. In the current invention, bioreactions and fermentations are used interchangeably; similarly, bioreactor and fermentor are used interchangeably.

In many chemical reactions, especially biological reactions, and more particularly in aerobic fermentation reactions, a persistent foam is generated, at least during a portion of the reaction time. This may occur for a variety of reasons, some of which are not fully understood. In some of these reactions, oxygen has to be continuously sparged into the bulk fermentation liquor, either as air or as concentrated oxygen, to satisfy the demand of certain types of aerobic bacteria. In fact, the aeration gas volume introduced to meet the oxygen demand of some of these aerobic bacteria is often sufficiently high that the associated foam causes metabolic shifts and release of products for which the bacteria are not highly suited.

For terminology clarity, the foaming phenomenon dealt with here typically occurs in a batch-type reaction system. The reactor vessel is typically a closed vessel with at least a majority of the volume occupied by the bulk liquor, where an active agent, particularly a specially-selected bacterial strain, reacts with at least one reactant in the bulk liquor. The reaction products are released into the bulk liquor. In some cases, as in the well-known fermentation of glucose to ethanol by yeast, the produced carbon dioxide forms bubbles that rise to the upper surface of the bulk liquor, where the bubbles will break, releasing the carbon dioxide into a headspace of the reactor. However, in some instances, the interaction of buoyancy and surface tension forces in the bubble at the interface of the bulk liquor and the headspace cause the bubble to not burst, establishing a persistent foam. This persistent foam has a gas volume to liquid volume ratio that is much higher than that found in the bulk liquor. Because of this high ratio of gas to liquid, the liquid phase in the persistent foam is essentially web-like. Left unchecked, this persistent foam can expand to substantially fill the headspace. Bubbles of air (or oxygen) introduced into the bulk liquor can also establish a persistent foam in the same manner as the bubbles of carbon dioxide can in an anaerobic fermentation.

The resolution of persistent foam by introducing—antifoaming/defoaming agents, which may be surface-active agents, at the top of the bulk liquor is well-known, but it is extremely undesirable in bioreactions and fine chemical reactions. The agents can be deleterious to the product and will need to be removed during isolating the products of the reaction.

In bioreactors of this type, it is also known that the reaction often proceeds from a starting material through a metabolic pathway in which one or more metabolites are produced before the final product, which in many cases is the desired product. However, in certain circumstances, there may be an interest in isolating one or more of these intermediate metabolites, as well as other products that may be released by the active microorganism. It is desirable to facilitate rapid, and at least semiautomatic, monitoring and measuring of these metabolites or other products. In some cases, the desired metabolite may be present during a short stage of the growth cycle of the producing microorganism. This short-lived event may be missed when the analyst uses standard bioreactors or fermentors. The short life of the metabolite produced at a stage of microbial growth may be destroyed by degradative enzymes released at a later stage of the growth of the same microorganism. Therefore, relying on conventional flask or bioreactor fermentation will not allow isolating the short-lived intermediate metabolite. An invention to remove and separate these metabolites not only provides the means to mass-produce novel bioreaction products, it also minimizes end-product feed-back inhibition, thus speeding the metabolic processes leading to these products.

It is thus an object of the present invention to provide a bioreactor system that will physically deal with persistent foams, determine the presence of short-lived metabolites, and facilitate the isolation and purification of these metabolites. These objectives are not presently met by the known prior art bioreactors.

SUMMARY

This and other unmet advantages are provided by the apparatus and method described and shown in more detail below.

In one embodiment, the apparatus for producing a target metabolite in a bioreaction, comprises a reactor vessel, a water bath, a foam collector and a reaction control console. The reactor vessel is sized to contain a bulk liquor in which the bioreaction is conducted with a headspace maintained above the bulk liquor. The water bath is arranged for controlling temperature in the reactor vessel, under control of the reaction control console, which is in communication with at least the reactor vessel and the water bath to monitor and control the bioreaction. The foam collector is arranged to receive a foam formed at an interface of the bulk liquor and the headspace and to break the received foam into a condensed foam liquid.

In some embodiments, the apparatus further comprises a fraction collector unit, arranged for withdrawing and analyzing samples from the reactor vessel; as well as a cooling system, arranged for controlling temperature in the fraction collector.

In many embodiments, the apparatus further comprises one or more analytical probes, arranged in the reactor vessel, means for agitating the bulk liquor and means for injecting one or more gases into the bulk liquor.

In some embodiments, the method for producing and concentrating a target metabolite from a bioreaction has the steps of: conducting the bioreaction with a selected microorganism in a bulk liquor of a reactor system having a headspace above the bulk liquor, under conditions predetermined to induce a persistent foam at an interface of the bulk liquor and the headspace; determining the presence of the target metabolite in the persistent foam; producing a condensed foam liquid by removing the persistent foam from the bioreactor and breaking the foam; and isolating the target metabolite from the condensed foam liquid.

In these embodiments, the target metabolite is preferentially partitioned into the persistent foam.

In one specific example, the target metabolite is paenibacillin or amyloliquecidin GF610. Both of these are newly-discovered antimicrobial peptides which are amphiphilic.

The step of producing the condensed foam liquid is preferably achieved in a foam collector.

The step of determining the presence of the target metabolite is achieved by at least one of: elapsed time of the bioreaction; measurement of at least one operating parameter of the bulk liquor selected from the group consisting of: dissolved oxygen, pH, temperature and turbidity; and a positive reaction to a predetermined bioindicator, typically provided by an inhibition of the bioindicator.

In many embodiments, the step of producing the condensed foam liquid comprises the sub-step of filtering the condensed foam liquid to remove the microorganisms.

In some embodiments, a foam collection device of the type described herein may be efficaciously retrofitted to prior art bioreactors to isolate and concentrate a target moiety generated in a bioreaction.

In achieving these advantages, the device and method intentionally induces or enhances foaming. By doing this, it has been seen that metabolites, such as, for exemplary reasons only, paenibacillin, have an amphiphilic nature that allows partitioning into the foam and separation. The separation has heretofore been difficult, due to the scarcity or physico-chemical properties of the metabolites. Paenibacillin is a potent antimicrobial peptide which is produced in micromolar quantities that can only be separated and purified from a medium through complex chromatographic techniques. Another example of metabolites that are readily partitioned in the foam is amyloliquecidin GF610, a newly-discovered two-component antimicrobial lantibiotic.

BRIEF DESCRIPTION OF THE DRAWINGS

A better understanding of the disclosed embodiments will be obtained from a reading of the detailed description and the accompanying drawings wherein identical reference numerals refer to identical parts and in which.

DETAILED DESCRIPTION OF A PREFERRED EMBODIMENT

Figure 1:
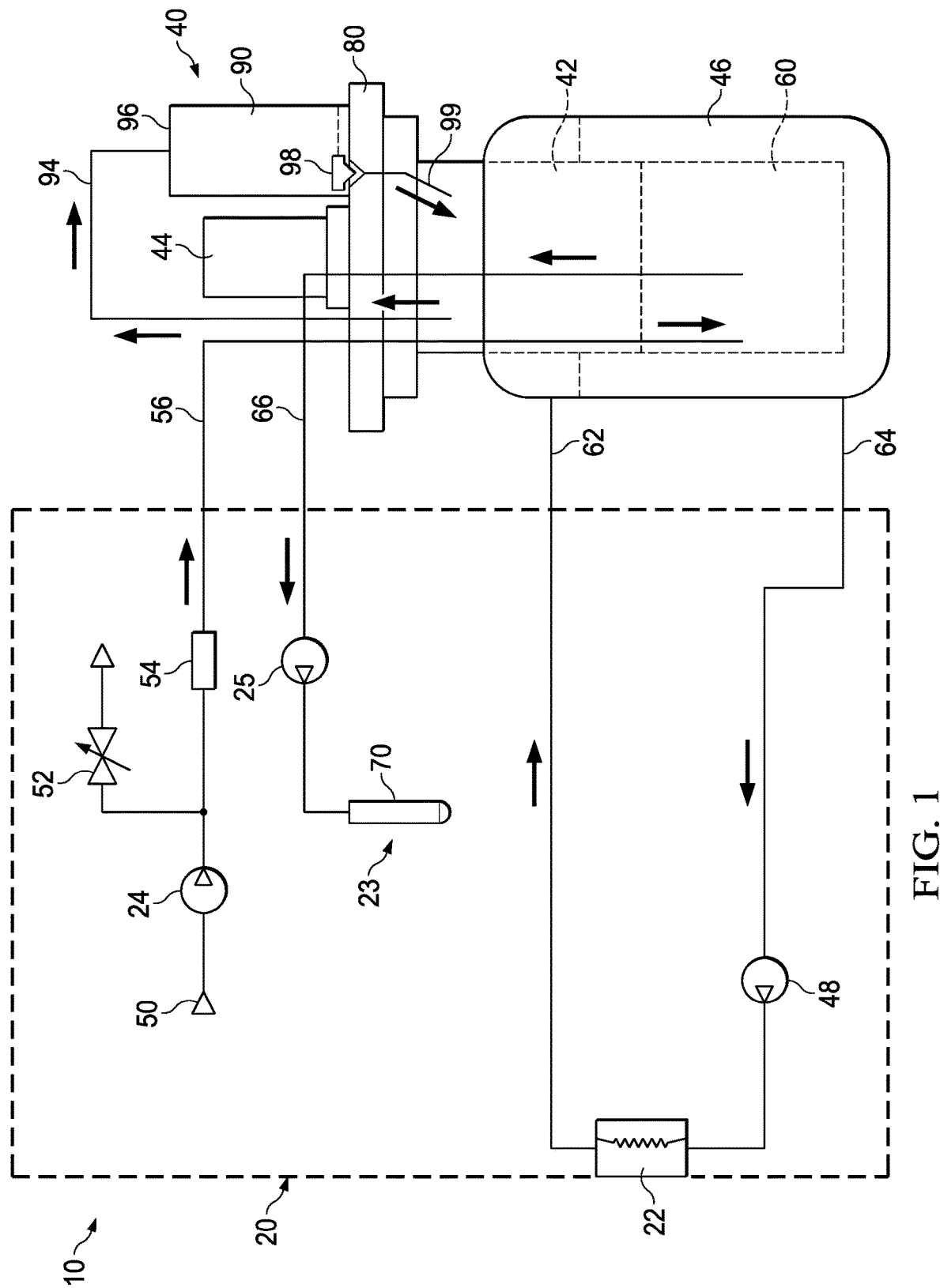
FIG. 1 is a schematic depiction of an embodiment of the bioreactor system incorporating the inventive concept.

The present invention is premised upon the discovery that, at least in certain selected circumstances, the metabolic products that are desired to be isolated can be partitioned in the liquid portion of a persistent foam. Thus, a bioreactor system that can determine the presence of the desired metabolite and can isolate a persistent foam from the bulk liquor provides capabilities not previously available in the prior art. The determination of the presence of the metabolite is based upon one or more of several grounds, including, but not limited to, rapid bioassay and/or predetermined biokinetics.

Some of the desired products are beneficial antimicrobial agents which may be produced by a microbial strain during a short stage within the growth cycle of the producing microorganism. The modifications provided by the embodiments of the present invention allow samples to be collected at precise intervals during the bioreaction cycle (e.g., growth of a microorganism). These samples are then processed in real time, and the presence of any active ingredient is determined by combining the sample with an appropriate bio-indicator. For example, the presence of a new antimicrobial agent synthesized at, for example, the $8^{th}$ hour of a 24-hour fermentation is facilitated by collecting a sample around that time, micro-filtering the sample, and mixing the filtered sample with a bacterium that is sensitive to the antimicrobial agent, that is, a bio-indicator. In the preferred embodiments, all of these steps are automated and under control of a processor unit.

The partition of certain bioactive metabolites in the persistent foam may occur by a preferential production in the foam, by a physical process that favors the presence of the metabolite at the interface between the bulk liquor and the headspace, or by another mechanism that is not fully understood. In any case, the metabolites formed during aerated bioreactions (by highly aerobic bacteria) tend to be amphiphilic agents (e.g., antimicrobial peptides). While the prior art, both in theory and practice, encourages steps to avoid foam formation during all types of fermentations, the embodiments taught herein collect the foam and return it safely and aseptically to the fermenting bulk liquor. Furthermore, the embodiments can collect the foam separately and allow the agents present in the foam to be harvested from this more concentrated source. The embodiments of the system disclosed here allow the detection and collection of rare active metabolites that have affinity for gas-aqueous interfaces in fermentations.

The embodiments of the bioreactor system are preferably provided with an optical probe comprising a precisely-spaced light emitter and detector. While the optical probes of this type are known, they are used in the embodiments of the present invention in a novel manner. The probe is immersed into the bioreactor to sense, in real time, the progression of the biological activity. The probe then sends a signal to a monitor or computer for viewing, storage or processing. The probe signal can be converted into a useful parameter such as optical density. When the bioreactor is used to grow a microorganism, the probe readings correspond to medium turbidity which is a measure of cell density. Other useful probes in this aspect are probes that measure changes in redox potential during bioreaction.

Fermentors and other bioreaction equipment are often heavily laden with features, many of which are rarely used. However, these systems lack the ability to monitor important secondary metabolites, such as antimicrobial agents, which are often synthesized at certain stages of microbial growth cycle and released from the producer cell in minute amounts. Fermentation processes are often so complex that intricate tasks, as those just described, are difficult to monitor or control. It is also often difficult to get the microorganism to respond in the same way with each fermentation because so many factors affect production of secondary metabolites. Obvious fermentation parameters such as air flow, temperature, and substrate feed are relatively easy to control, but so many other parameters are yet to be discovered and tracked.

Figure 2:
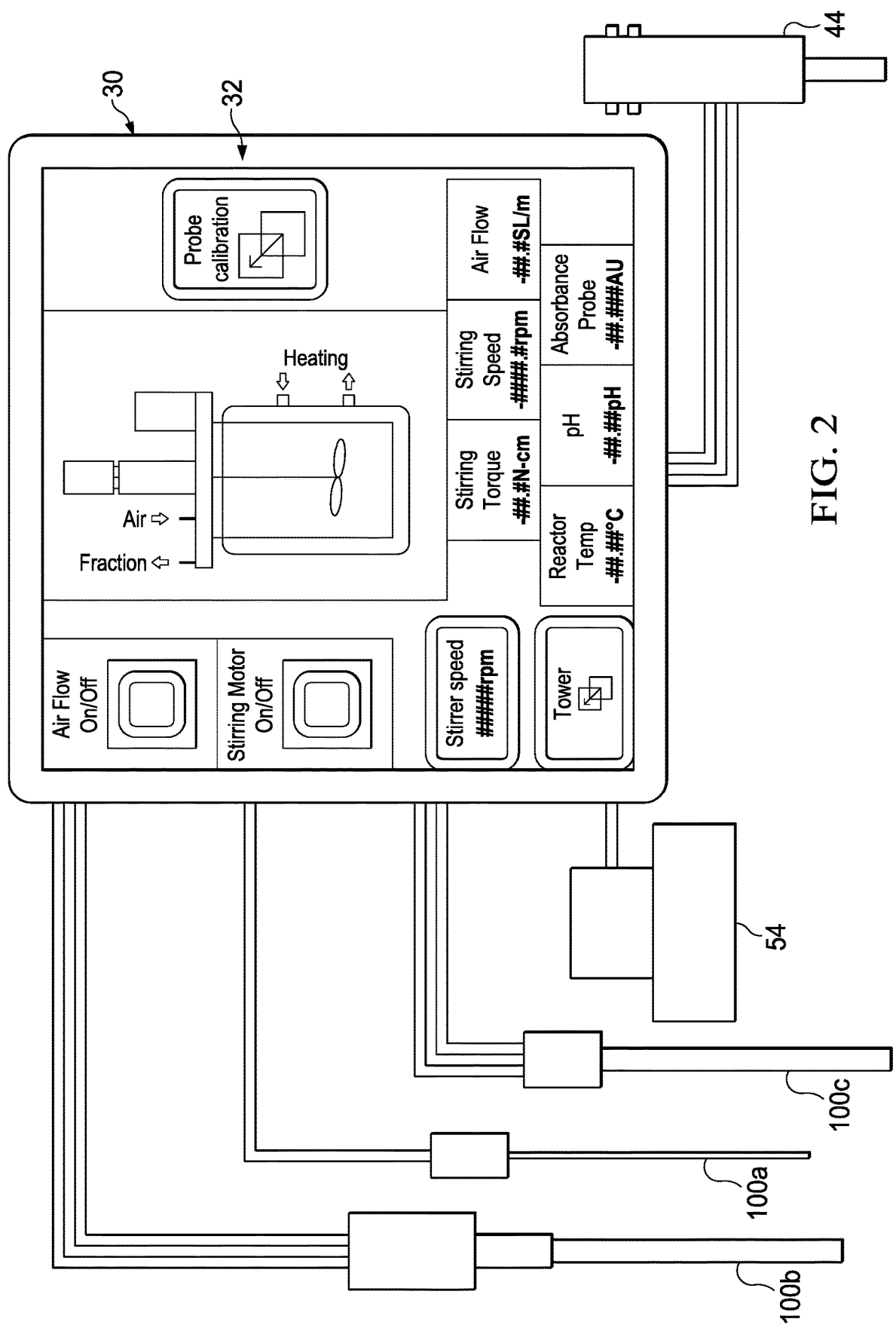
FIG. 2 is a schematic depiction of the control instrumentation of the bioreactor system.

As shown in the schematic depictions in FIGS. 1 and 2, a preferred bioreactor system 10 of the inventive concept integrates a number of components into a tower enclosure 20. Physical components in the tower 20 include a heated water bath 22, a refrigerated compartment to contain a fraction collector 23, an air pump 24, a peristaltic pump 25, and a console 30, which is depicted in FIG. 2. The console 30 preferably comprises a programmable logic controller (PLC) 32 with a touch-screen for instruction entry. Apart from the tower enclosure 20 is a reactor assembly 40 with a reactor jar 42, equipped with stirring means, preferably a magnetic drive agitator 44. The reactor assembly 40 is preferably attached to the tower enclosure 20 through quick-connect fittings.

The console 30 is the main user interface, and it provides an interface to control bioreaction temperature, air flow, stirring speed and fraction collection. In one embodiment, the control unit 32 uses a Horner XL6 programmable logic controller, commercially available from Horner APG Canada, of Calgary, Alberta. Inputs/outputs on the PLC include two Pulse Width Modulation (PWM) outputs to control the fraction collector motors. Also included are analog inputs for temperature sensors, an RS-232 communication port to communicate with the water bath controller, and digital outputs for miscellaneous controls such as air pump and stirring motor. PLC 32 is connected to various probes, such as thermocouple 100a, pH probe 100b and light absorbance measuring probe 100c, as well as air pump 24 and magnetic stirrer 44, to monitor and manage the bioreaction.

Beyond the control functions provided by the console 30, the tower enclosure 20 provides air and heat to the reactor assembly 40. Specifically, the air pump 24 has an air inlet 50, which preferably filters the incoming air, a flow control valve 52 and a flow meter 54. Output air passes via conduit 56 through a top of the reactor jar 42 and is injected below a surface of the bulk liquor 60 in the reactor jar.

In a similar manner, the water bath 22 is a part of a recirculating water system that supplies heated water to a reactor jacket 46, with the system also containing a water pump 48. Conduits 62 and 64 provide water flow to and from the reactor jacket 46. In many aspects of the invention, the water bath 22 is housed in the tower enclosure. The water bath 22 should include a thermostat, which is provided with a control interface to the PLC 32. In preferred embodiments, only the ports to fill the bath with water and to connect it to the bioreactor for fluid circulation are visible on the tower 20. By providing a sealed system, the water bath 22 allows the unit to be moved without the water splashing out and ruining any electronics.

Figure 3:
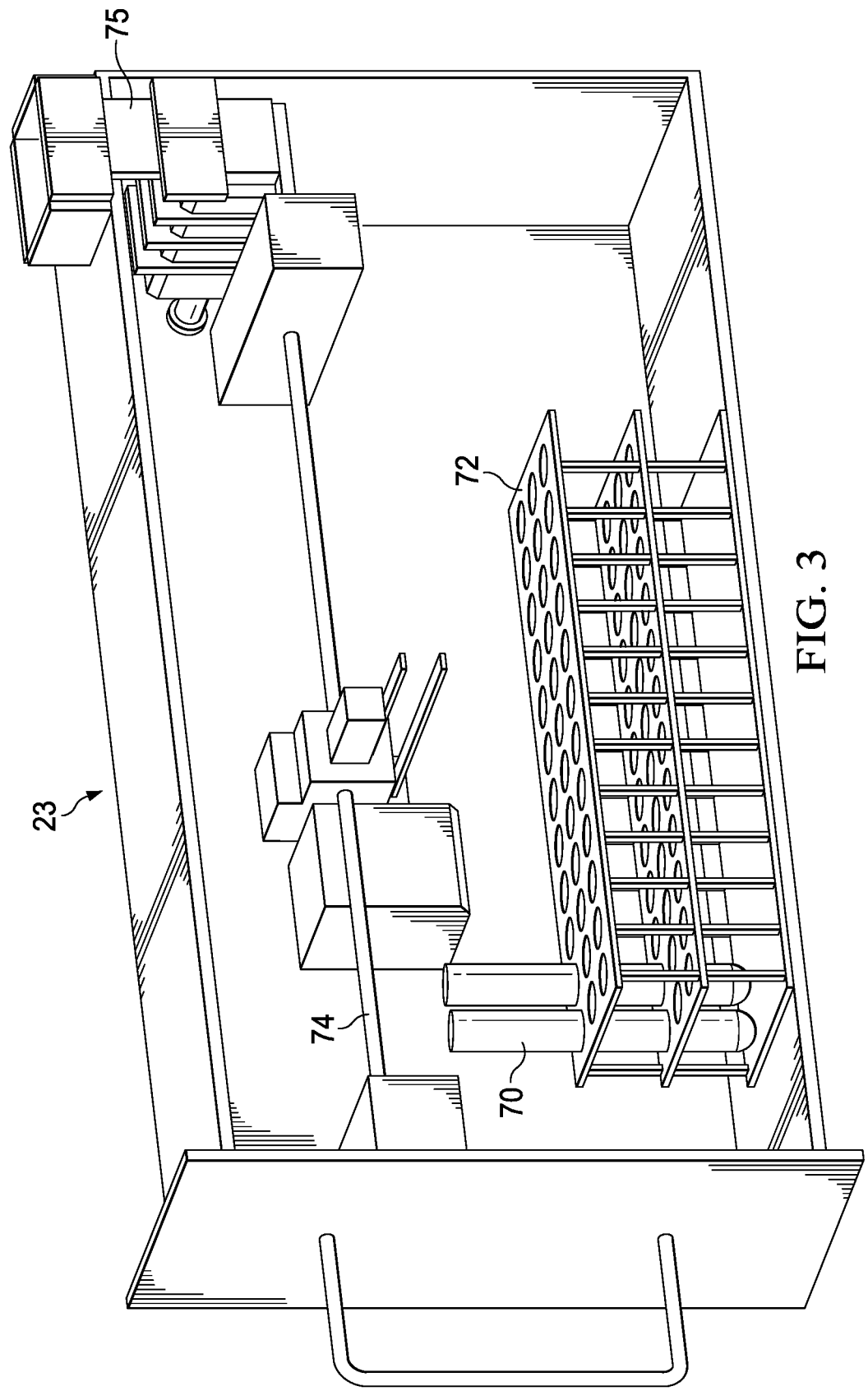
FIG. 3 is a detailed side view of a fraction collector portion of the bioreactor system.

The fraction collector 23 is housed in the tower enclosure 20, preferably in a refrigerated compartment thereof. The fraction collector 23 is schematically depicted in FIG. 1 by a test tube 70, the peristaltic pump 25, and the conduit 66 which draws samples from the bulk liquor 60 through the peristaltic pump to the test tube. More detail of an exemplary embodiment of the fraction collector 23 is shown in FIG. 3. This embodiment accommodates a rack 72 for accommodating a plurality of test tubes 70, preferably up to seventy-two such test tubes of a typical size of 13-mm. In the depicted embodiment, a filling arm 74 is precisely positioned above a test tube by stepper motors under the control of the PWM outputs of the PLC 32. The fraction collector 23 is embedded into an insulated enclosure equipped with a controllable cooling means, preferably a Peltier device 75, to maintain temperatures of around 4° C. The Peltier device is electrically powered and generates a hot and a cold side, each of which is fixed to a heat exchanger and two DC brushless fans used to move the heated or cooled air. As the first fan removes the hot air to the exterior of the tower enclosure, the second fan circulates air in the fraction collector past the cooling plate of the Peltier device.

Figure 4:
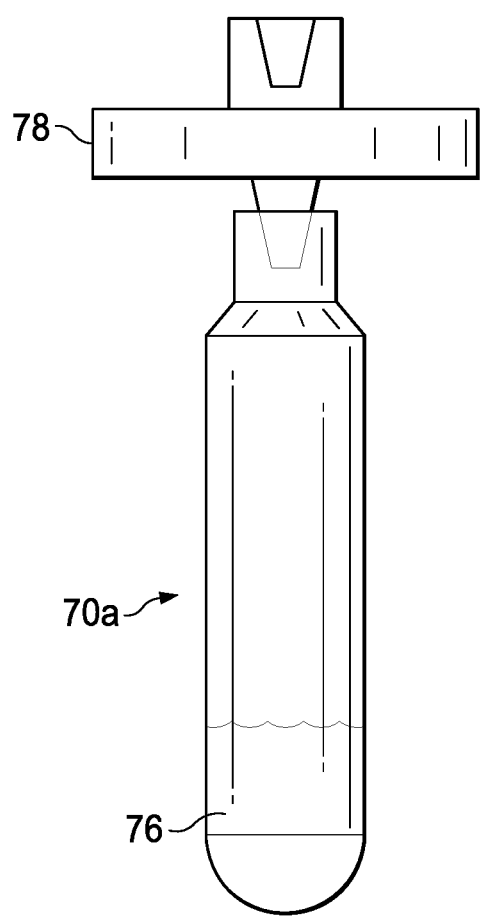
FIG. 4 is a side view of a bioindicator tube.

In a preferred version of the fraction collector 23, a speedy bioassay is achieved by collecting the fractions directly into a bioindicator tube 70a that is partially filled with a suitable bioindicator. Such a bioindicator tube 70a is depicted in FIG. 4. A good example of a bioindicator 76 for the bioindicator tube 70a is a cell suspension of a bacterium that is sensitive to the antimicrobial produced during the fermentation. Examples of bacterial bioindicators include *Escherichia coli* K12 and *Listeria innocua*. A top portion of the bioindicator tube 70a is fitted with a microfilter cartridge 78 to separate microbial cells from the collected fraction of the fermentation liquor that potentially contains the desired secondary metabolite. This design gives quick indication of when the antimicrobial compound is produced in the microbial growth cycle. In at least some of the embodiments, LUER-LOK-type fittings are used to connect each bioindicator tube with a dispensing tube of the fraction collector 23. A vertical axis on the fraction collector allows for this quick coupling. A rack cover may be used to hold all the tubes and filters, so that the fraction rack can easily detach after filling is complete.

A preferred manner of removing a desired fraction volume from the bioreactor is a peristaltic pump 25, which may be located exterior to the tower. The peristaltic pump 25 is controlled by the PLC 32. Tubing will be connected directly from the bioreactor vessel 42 to the fraction collector 23.

Referring back to FIGS. 1 and 2, details of the bioreactor assembly are shown. The bioreactor vessel or jar 42 is, in preferred embodiments, primarily made out of glass, with sufficient volume to contain about 6 liters of the bulk liquor 60. A lid 80 of the bioreactor would preferably be stainless steel, or another material for the ability to be sterilized or autoclaved. The lid 80 may be clamped onto a flange at the top of the bioreactor vessel, such as by using an O-ring gasket to seal the facing surfaces. The lid 80 is provided with a plurality of openings for microbial inoculation, sample collection, probe and thermocouple insertion, foam collector interface, etc. The bioreactor jar 42 will be easily disconnected from the tower 20 for autoclaving. A reactor jacket 46 may be provided for selectively heating or cooling the bioreactor vessel 42. Input and output ports of the water jacket may be coupled directly to a compression fitting for connecting the water jacket to the reservoir in the bioreactor tower.

The preferred manner of agitating the bulk liquor 60 in a sealed bioreactor vessel 42 may be a stirring propeller in the bioreactor, coupled magnetically to a stirring motor 44 external to the bioreactor vessel. Such a system eliminates a rotational seal that would tend to leak over time. The magnetic stirring motor 44 allows for a stationary seal on the lid and will have minimal leaking after repeated autoclaving. The motor 44 will be easily detached so the unit with the impeller in place can easily be autoclaved.

A known problem in conducting aerobic bioreaction is the need to provide air, with or without enhanced oxygen content, into the fermenting medium. As described above, the tower enclosure 20 has an air pump 24 for providing this air to the reactor jar 42. Excess air also needs to be vented out to avoid pressurization of the bioreactor vessel. Adding air while stirring the bulk liquor of a bioreactor can lead to the problematic or desirable foaming described above.

Figure 5:
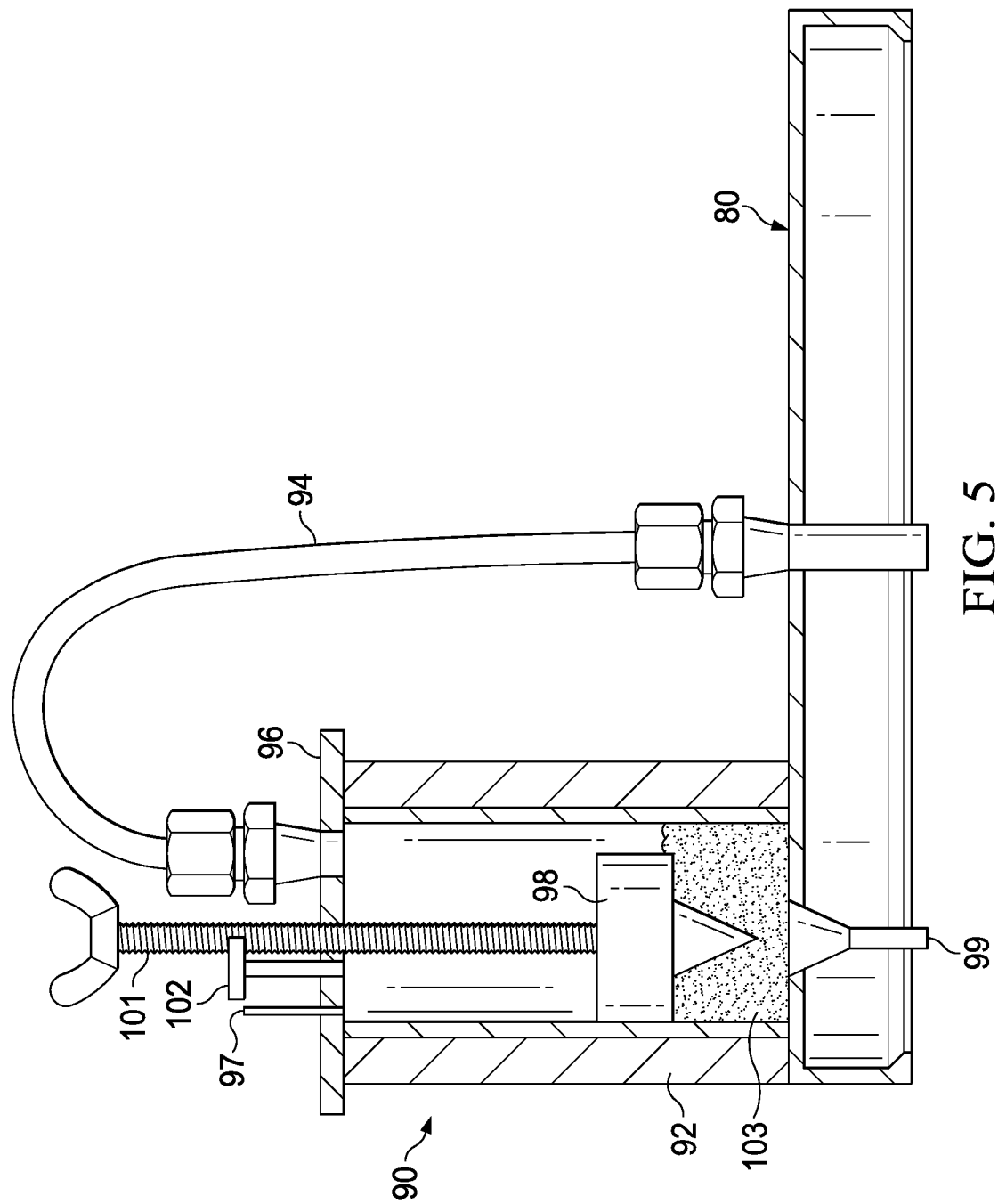
FIG. 5 is a sectional perspective view of a foam collector vessel.
Figure 7:
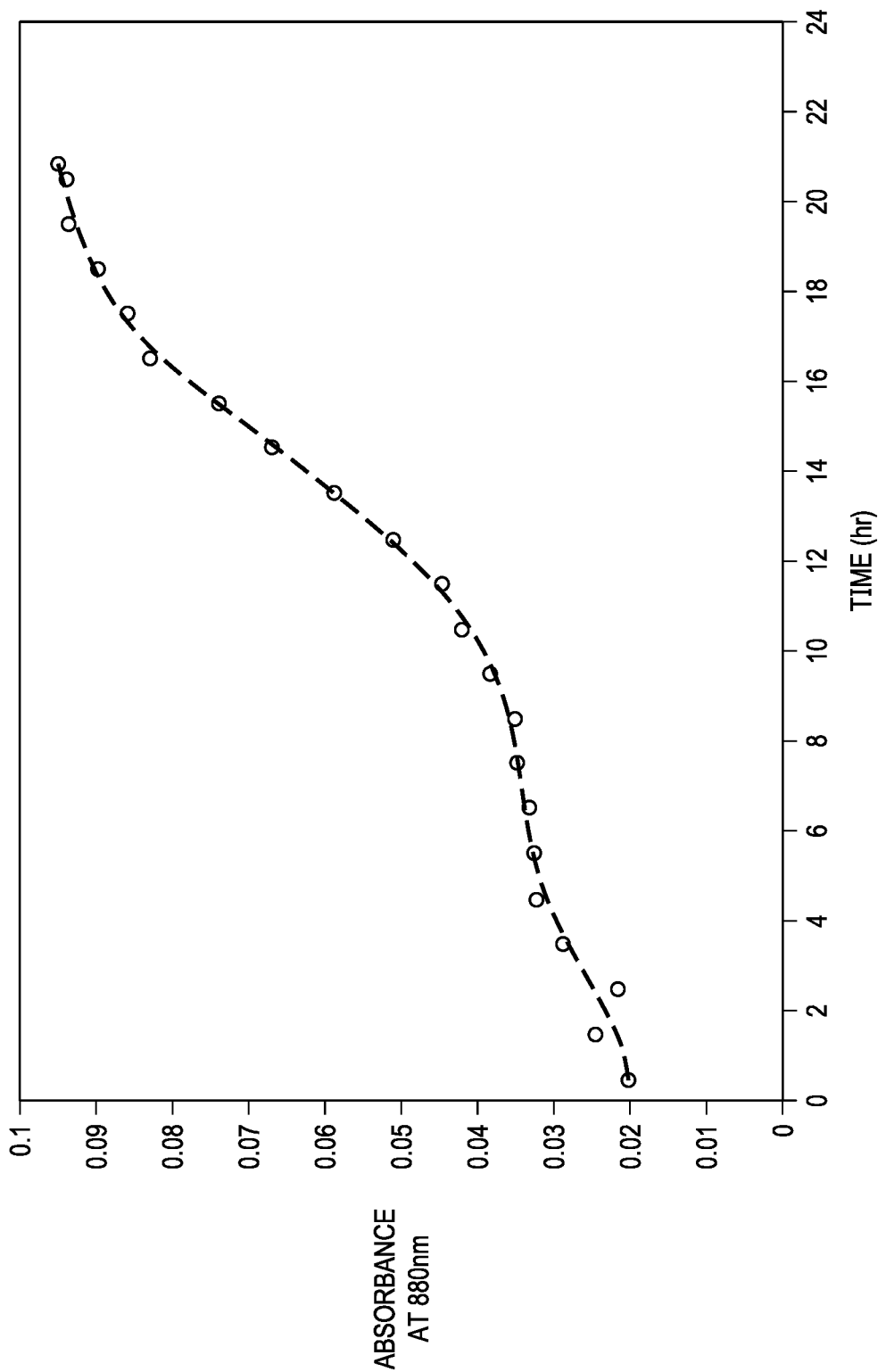
FIG. 7 is a graph in which light absorbance at 880 nm is plotted against time for an experiment demonstrating use of the bioreactor system for producing paenibacillin.

The preferred embodiments of the present invention are provided with a foam collector 90, located on or near the lid of the bioreactor vessel 42, as seen in more detail in FIG. 5. It is desirable to provide a jacket 92 to the foam collector 90 for temperature control. Heating may be used to maintain condensed foam in the collector 90 at the fermentation temperature, and cooling may be used to assist in breaking a persistent foam into a condensed form. As seen in FIG. 1, a conduit 94 allows foam from the reactor vessel 42 to enter the top 96 of the foam collector, where an opening 97 is used to vent pressure that may build up during this process. A float valve 98, located inside the collector 90, can be selectively opened or closed as a selected amount of condensed foam accumulates in the collector. In this manner, condensed foam may be either returned to the bulk liquor 60 through conduit 99 or drawn off for analysis or separation of desired product. This foam collector can also be manually plugged to allow foam collection by tightening float adjustment screw 101, pushing the float to the closed position. Collected foam 103 can then be retrieved by syringe through the septum 102 on the foam collector lid.

Figure 6:
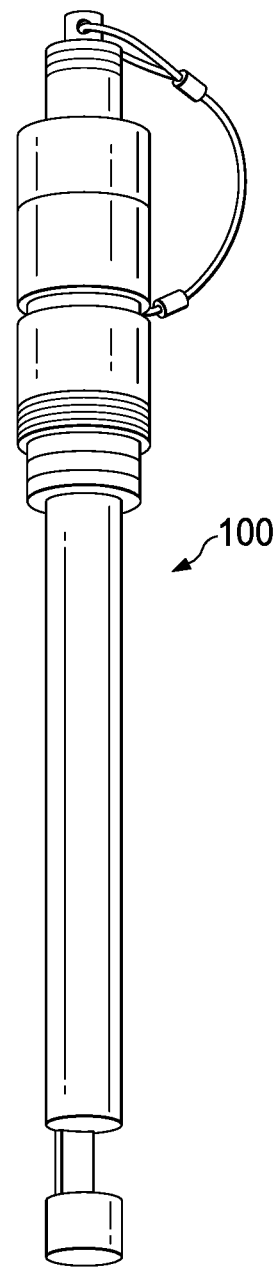
FIG. 6 is a side elevation view of an analytical probe.

It will also be desirable to provide the bioreactor vessel 42 with at least one probe in contact with the bulk liquor 60 for monitoring and analyzing conditions of the bioreactions being conducted. A typical probe 100 of this type is depicted in FIG. 6. A number of commercially available probes will be useful for this purpose, many of which will be multi-functional. Temperature may be measured by a thermocouple 100a, pH by a pH probe 100b, absorbance by an absorbance meter 100c and these will be tracked with respect to time through connection to PLC 32, as shown in FIG. 2. Dissolved oxygen is another parameter that can be monitored. The probe 100 is easily disconnected and can be capped and autoclaved. This allows a proper probe (or plurality of probes) 100 to be used, appropriate to the reaction being conducted. The probe 100 also comes with a display meter that will display current reading and allow real time monitoring of the bioreaction process.

A fermentation run was carried out using *Paenibacillus polymyxa* OSY-DF, a highly aerobic bacterium that produces the antimicrobial peptide, paenibacillin.

In the experiment conducted, the growth of the microorganism was successfully recorded using the bioreactor system described herein. Two liters of reconstituted milk powder (10%) was used as the growth medium for paenibacillin production. Airflow was set at 2.3 liters per minute and the stirring speed was 72 rpm. The temperature was maintained at 30° C. Data were collected at the rate of one set of readings per minute. A sample of the data, particularly, absorbance at 880 nm, is presented in FIG. 7, covering a period of approximately 21 hours. These data reveal that the microorganism's growth occurred in a bi-phasic manner, and the production of paenibacillin occurred mainly at the middle of the second phase. The ability of the bioreactor disclosed herein to monitor the growth and production in a turbid medium, such as the milk, is considered to be unprecedented.

In conducting a separate experiment, the fermentate and foam were collected separately from the bioreactor and the foam collector, respectively. Both the fermentate and the foam (in the form of condensed foam liquid) were centrifuged to remove bacterial cells. The cell-free centrifugation supernatants were mixed with XAD-7HD resin (10%) and absorption of paenibacillin to the resin was allowed during 24 hours of holding. The resin was washed and the paenibacillin was eluded from the resin, using 75% ethanol. Most of the ethanol was evaporated, and residues were resuspended in water resulting in 2× concentrated fermentation extract and foam extract. Each of the two extracts was spotted (10 μl each) onto a lawn of an indicator bacterium (*Listeria innocua*) embedded in a layer of soft agar. Review of the agar after an appropriate incubation period showed that the fermentation extract provided a clear zone of inhibition, but that the zones appearing where the foam extract was spotted to the agar are distinctly much larger and clearer. It is qualitatively estimated that the antimicrobial activity in the foam extract is on the order of at least 20 times greater than that observed in the fermentate extract.

This result was quantitatively confirmed in another experiment. In that experiment, a fermentation run of approximately 24 hours duration was conducted at 30° C., in which Tryptic Soy Broth (TSB) was fermented with *Paenibacillus polymyxa* OSY-DF. In a first run, in which the foam collector was not used, paenibacillin concentration in the final bulk solution was 32 μg/ml. However, in a second run conducted using the foam collector, the paenibacillin concentration in the bulk solution was only 4 μg/ml, with the concentration in the foam collector was 132 μg/ml, a concentration 33 times greater than the concentration in the bulk solution. More recent and more detailed testing involving paenibacillin is provided below.

In another experiment using a *Bacillus velezensis* GF610 which produces the two-component antimicrobial lantibiotic, amyloliquecidin GF610, the foam contained the antimicrobial agent in a concentrated form whereas the bulk medium contained the agent at much lower concentration.

Paenibacillin is a novel antimicrobial lantibiotic suitable for testing the efficacy of the inventive bioreactor. It is amphiphilic, highly water soluble and has relatively high temperature and pH stability compared to commercially available lantibiotics such as nisin. It is potent against Gram-positive bacteria including species of *Listeria, Clostridium, Lactobacillus, Staphylococcus, Bacillus*. The broad antimicrobial coverage and desirable physico-chemical characteristics make paenibacillin suitable for future applications in the preservation of food, cosmetics and other perishable products. The wild strain, *P. polymyxa* OSY-DF, produces the antimicrobial agent variably; therefore, an alternate strain, OSY-EC, that produces the antimicrobial on a consistent basis has been developed. This strain was isolated after screening for spontaneous mutants resistant to selected antibiotics that target protein synthesis mechanism. Despite the enhancement achieved through strain selection, there is a need for improving the recovery of paenibacillin produced in microbiological and industrial media.

Producing metabolites by aerobic microorganisms often involves vigorous stirring and air bubbling. This results in foam accumulation in the bioreactor, which is traditionally undesirable, due in large part to equipment inadequacies. It is now recognized that producing foam can be beneficial; and, with the inventive bioreactor, can even be utilized to separate and concentrate beneficial proteins and peptides. Introducing air through stirring increases air-water interface. Protein molecules with hydrophobic and hydrophilic regions (i.e., amphiphilic) in aerated bioreactions may accumulate at the interface and stabilize the foam. If the amphiphilic components in the bioreator include antimicrobial peptides, these also accumulate in the air-water interface, i.e., foam. Migration of these antimicrobials to the air-water interface not only concentrates these agents in bioreactor foam, but also may decrease product feedback inhibition.

Amphiphilic antimicrobial molecules have the potential to be removed by foam separation, as demonstrated by recovering nisin produced by *Lactococcus lactis*, and surfactin and iturin produced by *Bacillus subtilis*. However, very little of the prior work has studied foam collection from culture broth during the fermentation, mostly after bioreactions were completed, and none of that work dealt with aerobic bioreactions. Foaming not only concentrated the antimicrobials during the bioreaction, it also increased product yield. Nisin production was increased 36.2% when continuous foam recovery was used compared to traditional batch fermentation.

With this knowledge at hand, and an inventive bioreactor designed for dealing with fractionating antimicrobials, or other desirable target compounds, the research to optimize bioreactor conditions to maximize the fractionation into foamate (i.e., condensed foam) was undertaken.

Response surface methodology (RSM) has been used in the past to optimize the separation of bioactive peptides from hydrolyzed proteins, although optimization of antimicrobials produced by bacteria during fermentation using RSM has not been reported in the known literature. The separation of nisin by foam fractionation has been optimized through a one-factor-at-a-time methodology, but that optimization technique is not as efficient as RSM.

An optimization study should include determining optimal levels of crucial factors. Typical factors to be considered are pH, temperature, and aeration, using statistical design of experiments (DOE). Methods based on DOE are more complicated than the one-factor-at-a-time approach, but are more time and resource efficient. Unless the fermentation or bioreaction is already operating at maximum productivity, which is likely not the case, DOE can improve the process.

The study was undertaken to determine if paenibacillin could be separated efficiently in foam, and if so, could the titer and yield be improved in foamate generated during antimicrobial production. If successfully recovered in foamate, the paenibacillin could be recovered downstream of the bioreactor in fewer steps, making large-scale production more economically viable.

*P. polymyxa* OSY-EC was used to produce paenibacillin. *Listeria innocua* ATCC 33090 was used as a sensitive bioassay indicator to determine paenibacillin concentration, due to paenibacillin's known inactivation of Gram-positive bacteria. The stocks of these strains were prepared in 40% glycerol medium and stored at −80° C. until used in the experiments.

*P. polymyxa* OSY-EC were cultured in TSB (Becton Dickinson, Franklin Lakes, N.J.) or TSB containing 0.6% yeast extract (TSBYE; Becton Dickinson). The bacterium was transferred in these media twice and incubated for 24 h at 30° C. before inoculation of the respective medium in the bioreactor. The bioreactor medium was inoculated, at 0.1% v/v level, with the prepared seed culture. *L. innocua* was cultured in TSB at 37° C. prior to use in paenibacillin bioassay.

Figure 8:
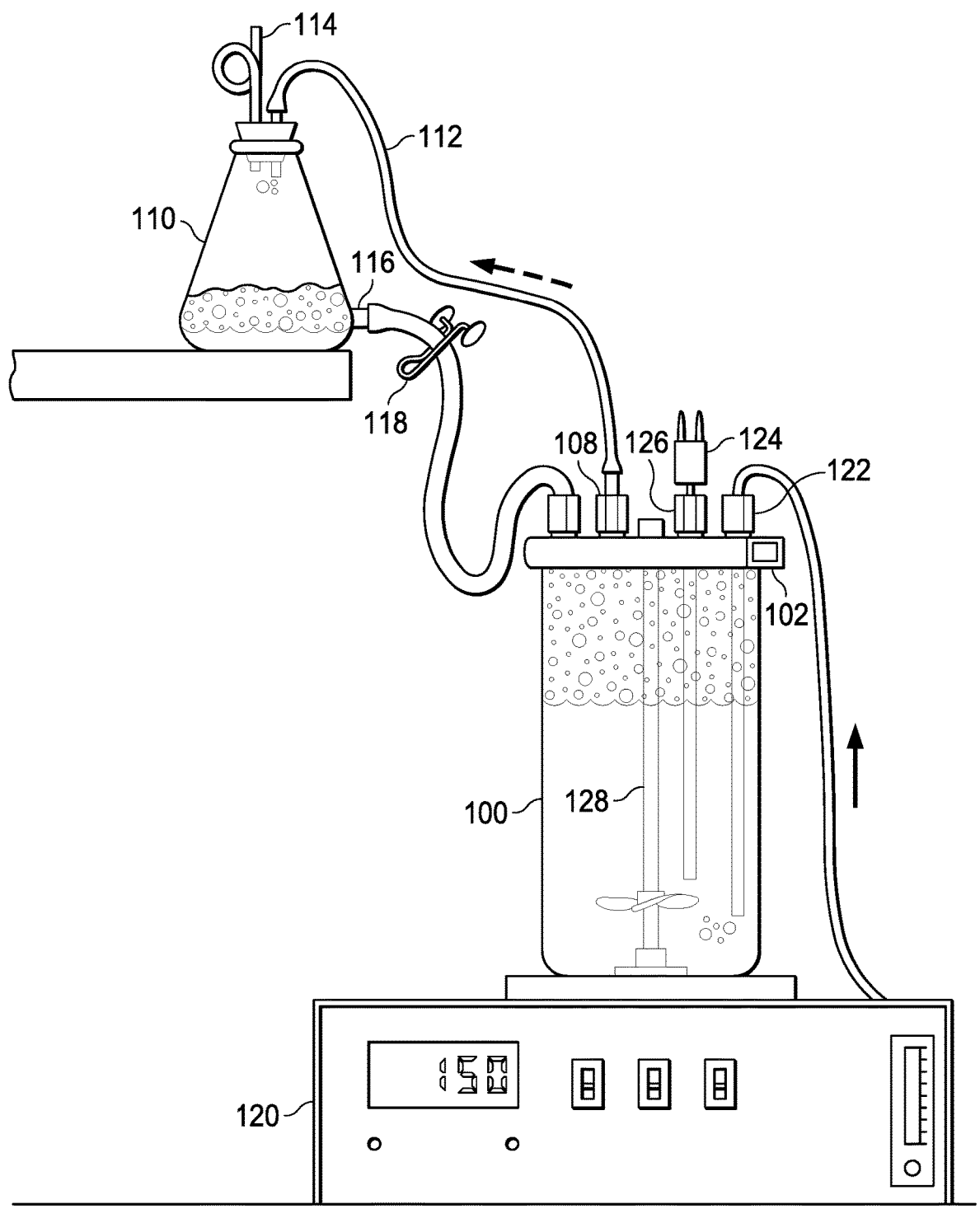
FIG. 8 is a schematic depiction of an experimental set-up for conducting a Response Surface Methodology (RSM) experimental design to optimize paenibacillin production.

The paenibacillin was produced on a 2-L bioreactor, mounted on a reactor base (VirTis omniculture; The Virtis Company, Inc., Gardiner, N.Y.). Atmospheric air was sterilized by a 0.45 µm filter before entering the bioreactor. A water bath was used to pump heated water through tubing within the bioreactor to obtain the desired incubation temperature. All reactions were run at 400 ml of TSB or TSBYE. The foam produced was collected throughout incubation in 1-L flasks connected by tubing to the top of the bioreactor 100, as seen in FIG. 8, which is described in more detail below. Two similar bioreactors were run side by side to increase run capacity. After incubation, the collected foamate and spent medium were centrifuged at 10,000×g for seven minutes at 4° C. to remove cells. The cell-free foamate and spent medium were stored at 4° C. until tested for antimicrobial concentration determination.

The 2-L bioreactor vessel 100 was modified to allow for foam collection, as shown in FIG. 8. The bioreactor lid 102 was sealed well with a gasket and clamp. Ports that were typically designed for easy plugging and plug removal, such as the inoculation port, were replaced with screw capped openings 106 that can hold pressure. The reactor vent was changed to a foam port 108 and it was connected to the top of the foam collection jar 110 by a tube 112. During the bioreaction run, a large volume of foam filled the head space and flowed out of the foam port 108, up the tube 112 to the top of the foam collection jar 110. The foam/air entered the foam collection jar and collapsed into foamate. Excess air left through the foam collection jar vent 114. The foam collection jar 110 also had a bottom port 116 that could be used to return foamate to the bioreactor vessel 100 or clamped off by clamp 118 when foamate collection was desired. A reactor control unit 120 regulated air flow to the bioreactor vessel 100 through port 122, controlled temperature in the bioreactor vessel through temperature data received from a thermocouple 124 in port 126, and stir speed of a stirrer 128.

In the initial screening tests, the approximate quantities of paenibacillin produced in bulk media or foamates were determined. Two 10 µl aliquots of cell-free bioreaction product were spotted on a soft TSA (containing 0.75% agar) overlay seeded with *L. innocua*. The diameters of the areas of inhibition (clearing) were measured after incubating the plates for 24 hours at 37° C. Larger area of inhibition indicated greater antimicrobial concentration in foamate.

Figure 9:
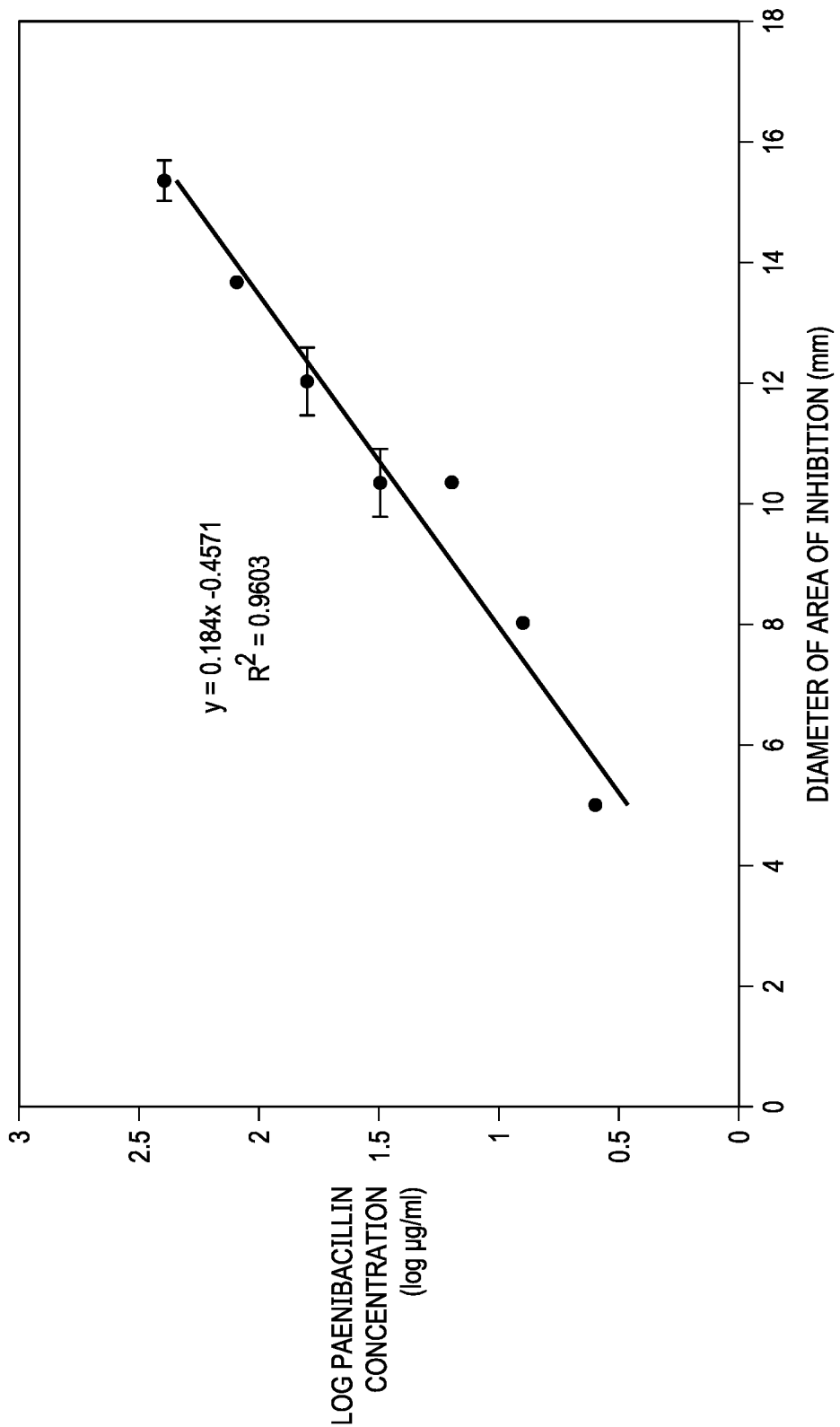
FIG. 9 is a standard curve for paenibacillin concentration ($\log_{10}$ μg/ml) vs. diameter (mm) of the area of inhibition of the indicator bacterium, *Listeria innocua*, wherein each point represents an average of three replicates.

Before calculating paenibacillin concentration, a dose-response standard curve, shown as FIG. 9, was constructed, by spotting known concentrations of paenibacillin on indicator-seeded soft agar overlay. The plates were then incubated, as described previously. The diameter of areas of inhibition were measured and plotted against the corresponding paenibacillin concentrations. Each point represented an average of three replicates. The equation that described the line of best fit was then used to calculate paenibacillin concentration in bulk media or foamates from the diameter of the corresponding inhibition areas.

During the final optimization of bioreaction conditions, paenibacillin production was quantified by a method modified from those described in prior art. Briefly, the cell-free bulk medium or foamate underwent two-fold serial dilutions and 10 μl aliquots were dispensed onto soft TSA seeded with *L. innocua*. The plates were incubated at 37° C. for 24 h. The prior art teaches that the minimum inhibitory concentration of paenibacillin against *L. innocua* is known to be 4 μg/mL. Therefore, and from knowing a dilution factor for the last dilution that shows inhibition, the concentrations of paenibacillin were calculable.

A partial factorial screening design was set up to investigate five factors, each at two levels. The factors were: media composition (TSB with or without yeast extract); temperature (30 or 36° C.), air flow (0 or 0.8 L/min), stir speed (300 or 500 revolution/min), and incubation time (16 or 24 h). A total of 20 tests, some of which were duplicate runs, were conducted. Of the tests, simultaneous incubations were performed in identical bioreactors. Paenibacillin concentration was determined in each case. If the paenibacillin concentration was determined to be below the threshold level of 4 μg/mL, the paenibacillin concentration was considered to be 0. Of the twenty tests run, four resulted in a non-zero paenibacillin concentration. Of these four, two of the tests were under identical conditions (TSB w/o yeast extract, 30° C., 0.8 L/min, 500 rpm, and 24 h), although the paenibacillin concentration was 470 μg/mL in one run and 200 μg/mL in the other. The other two non-zero results showed a paenibacillin concentration of 310 μg/mL (TSB with yeast extract, 30° C., 0.8 L/min, 300 rpm, and 24 h) and 250 μg/mL (TSB with yeast extract, 36° C., 0.8 L/min, 500 rpm, and 24 h). Known linear modelling techniques were used on the data to determine parameters for further experiments.

Based on the results of the screening model, the path of steepest assent was determined. The factors with significant effect were adjusted to improve antimicrobial concentration in the foamate. Airflow, stir speed and incubation time were varied together from the determined optimal step size to improve paenibacillin titer. The optimal conditions were then fine-tuned with RSM.

A two-level central composite design (CCD) was used to investigate the interaction of the significant factors near the optimum conditions. In this experimental design, incubation times varied in 1 h increments between 23 and 26 h, airflow was 1±0.2 LPM, and stir speed was set at 450, 500, 520 or 540 rpm. Two similar bioreactors were used to complete the study. The bioreactor utilized was recorded and included in the model if it had a significant effect. The optimal conditions of airflow, temperature and stir speed for bioreactions were calculated from the resulting model. Factors with significant effect only (p value <0.05) on paenibacillin concentration in the foamate were included. Results showed that airflow, time and stir speed had significant effects (p <0.05) on paenibacillin recovery in the collected collapsed foam (foamate). The optimal conditions for antimicrobial concentration in the foam were as follows: airflow of 0.95 LPM, incubation time of 23 h, and agitation speed of 450 RPM. These data are expected to improve the feasibility of commercial production and downstream processing of this novel antimicrobial peptide and the protection of food against pathogenic and spoilage bacteria.

It is notable in the CCD experiment that the paenibacillin concentration in the bulk media after the incubation did not meet or exceed the predetermined threshold level of 4 μg/mL, demonstrating partition of the paenibacillin produced into the foamate, where the threshold was exceeded (and significantly) in all but one of the twenty-three test runs.

Calculating the capacity coefficient allows application of the optimum conditions concluded in this study to other bioreactors, using methods described in the prior art by Fukuda et al. and also by Middleman. The airflow and stirring parameters along with volume and dimentions of bioreactor vessel were incorporated into determining the capacity coefficent, which describes the degree of saturation as a function of time.

The factors with significant effects on paenibacillin concentration affect different aspects of foam formation. Airflow and stir speed in the bioreactor affect incorporation of air into the media and incubation time affects the amount of time needed for foam to form. Stir speed and air flow influence foam formation and stability therefore affected the ability of foam to form and reach the collection jar, consistent with the prior art. Both methods of air incorporation needed to be balanced to have an amount of dissolved oxygen in the medium needed to induce bacterial metabolism leading to antimicrobial production. Bioreaction time was a significant factor because antimicrobials need time to be produced and migrate to the air-water interface.

Paenibacillin is a secondary metabolite. Therefore, production by *P. polymyxa* OSY-EC commences at the end of the exponential growth phase, so the antimicrobial agent was non-detectable in the foamate after the shorter incubations (16 h). Paenibacillin concentration in foamate was not significantly influenced by the investigated media and temperature. Both tested media supported the production of paenibacillin and foam formation. Considering the lack of observed media effect, it is likely that nutrient concentration was not a limiting factor in production of paenibacillin. The temperature range tested supported growth of the producer and production of paenibacillin in previous studies in the prior art. The factors with significant effect on paenibacillin concentration were further optimized to maximize paenibacillin titer and yield in foamate.

The ideal stir speed, airflow and incubation time were identified through RSM. The model developed described a saddle point, where paenibacillin concentration in foamate was a function of airflow, time, RPM and the bioreactor used. Different reaction parameters could be plugged into the model to predict paenibacillin production These parameters produced enough foam to carry the antimicrobial to the foam collection jar without diluting with excess microbiological media. It was likely that excessive foam formation diluted the paenibacillin in the foamate. Conversely, a small dense foam did not produce a large enough volume to be collected.

Concentration of paenibacillin in foamate ranged from 0 to 768 μg/ml. No antimicrobial activity was detected in the liquid media for any RSM run. This suggests total migration of the antimicrobial agent from the medium bulk to foam. A bioreaction under the optimal conditions, as predicted by the model, would produce 743 μg/ml paenibacillin in the foamate. Growth of *P. polymyxa* OSY-EC in the same bioreactor using TSB medium and the original bioreaction parameters (33° C. for 16 h incubation, 0.6 LPM air flow, and 300 RPM stirring speed), with no foam separation, produced paenibacillin at 16 μg/ml. The maximum concentration of paenibacillin produced (768 μg/ml of foamate) was a 48-fold increase in concentration of paenibacillin from original parameters. Increased concentration of paenibacillin in foamate diminishes the need for the expensive concentration and purification steps needed during downstream processing of bioreactor products.

The optimization process not only increased the migration of paenibacillin to the foam, it also increased the yield of the antimicrobial agent. In one 400-ml bioreaction, using what were considered to be optimized conditions, the paenibacillin production reached 12,672 µg as collected in foamate where paenibacillin production without foam removal reached 6,400 µg only. The almost double yield reported here could be due in part to lowered feedback inhibition, allowing the production of paenibacillin to continue uninhibited during the microbial bioreaction, but is notable. At the optimized production level, the 12,672 µg collected in the foamate represents almost 90% of a theoretical 14,206 µg total production. This also represents an enhancement of the concentration of the paenibacillin by a factor of better than 21 times. In a few additional non-optimzed tests, almost 85% and better than 73% of the theoretical paenibacillin production reported to the foamate, with respective concentration enhancements of 15 and 23 times. This concentration of the target compound in the foamate is not known to be reported in the prior art.

The results obtained are believed to be applicable to other bioreactors. The optimal airflow and stir speed parameters were incorporated into the calculation of the capacity coefficent, which can be compared between different bioreactors of different sizes, as taught by others. The capacity coefficient for the optimized conditions was $187\ s^{-1}$. If the current bioreaction is scaled up and the capacity coefficient is held constant, the paenibacillin titer in the formed foam is expected to remain at the high concentration reached in the current study.

Most bioreactors can be modified to collect foam with little difficulty. In this case, low-pressure feed lines may require check valves to prevent foam back-flow. The bioreactor can be easily set up as a continuous-feed or fed-batch reactor.

While the foregoing has described laboratory scale bioreactor applications of the invention and particularly the collection and condensation of persistent foam to concentrate products found in the liquid phase thereof, the concepts may be adapted to non-biological reactions carried out in an agitated bulk liquor, such as for the production of fine chemicals. In such a case, it may be desirable to scale-up the size of the reactor vessel to accommodate volumes on the order of 600 liters of bulk liquor instead of the 6-liter capacity described here. Other variations and modifications will be known to one of skill in the art and still be within the scope of the claimed invention.

What is claimed is:

1. An apparatus for producing a target metabolite in a bioreaction, comprising:
   a reactor vessel, sized to contain a bulk liquor in which the bioreaction is conducted with a headspace maintained above the bulk liquor;
   a water bath, arranged for controlling temperature in the reactor vessel;
   a reaction control console, in communication with at least the reactor vessel and the water bath to monitor and control the bioreaction; and
   a foam collector comprising:
      a reservoir for receiving foam, the foam being formed at an interface between the bulk liquor and the headspace, wherein the reservoir is exterior to the reactor vessel;
      a first conduit for transferring foam from the reactor vessel to the reservoir, wherein the first conduit is in fluid communication with the reservoir and the headspace within the reactor vessel;
      a second conduit for returning condensed foam liquid from the reservoir to the reactor vessel, the condensed foam liquid being formed when the transferred foam breaks, wherein the second conduit is in fluid communication with a lower portion of the reservoir and the reactor vessel; and
      a valve for selectively stopping or starting the flow of condensed foam liquid from the reservoir to the reactor vessel.

2. The apparatus of claim 1, further comprising:
   one or more analytical probes, arranged in the reactor vessel.

3. The apparatus of claim 1, further comprising:
   means for agitating the bulk liquor.

4. The apparatus of claim 1, further comprising:
   means for injecting one or more gases into the bulk liquor.

5. The apparatus of claim 1, wherein the valve is a float valve.

6. The apparatus of claim 1, wherein the foam collector further comprises a temperature control device for selectively heating or cooling the foam received in the reservoir to concentrate the foam.

7. The apparatus of claim 6, wherein the temperature control device for selectively heating or cooling the foam received in the reservoir is a jacket that surrounds the reservoir, wherein the jacket is exterior to the reactor vessel.

8. The apparatus of claim 1, further comprising an opening in an upper portion of the reservoir to vent gas pressure in the reservoir.

9. An apparatus for producing a target metabolite in a bioreaction, comprising:
   a reactor vessel, sized to contain a bulk liquor in which the bioreaction is conducted with a headspace maintained above the bulk liquor;
   a water bath, arranged for controlling temperature in the reactor vessel;
   a reaction control console, in communication with at least the reactor vessel and the water bath to monitor and control the bioreaction;
   a foam collector comprising:
      a reservoir for receiving foam, the foam being formed at an interface between the bulk liquor and the headspace, wherein the reservoir is exterior to the reactor vessel;
      a first conduit for transferring foam from the reactor vessel to the reservoir, wherein the first conduit is in fluid communication with the reservoir and the headspace within the reactor vessel;
      a second conduit for returning condensed foam liquid from the reservoir to the reactor vessel, the condensed foam liquid being formed when the transferred foam breaks, wherein the second conduit is in fluid communication with a lower portion of the reservoir and the reactor vessel; and
      a valve for selectively stopping or starting the flow of condensed foam liquid from the reservoir to the reactor vessel; and
   a fraction collector unit exterior to the reactor vessel comprising:
      at least one sample collection vessel for receiving a quantity of liquid;
      a dispenser for selectively dispensing quantities of liquid into sample collection vessels; and
      a pump configured to draw liquid from within the reactor vessel and transfer it to the dispenser.

10. The apparatus of claim 9, wherein:
    the dispenser comprises a moveable filling arm and a dispensing tube; and the moveable filling arm is configured to move the dispensing tube into position above a sample collection vessel so that liquid from the dispensing tube can be dispensed into it.

11. The apparatus of claim 9, wherein the at least one collection vessel comprises a bioindicator tube that is partially filled with a bioindicator that is suitable for screening for a compound produced during a bioreaction conducted in the reactor vessel.

12. The apparatus of claim 11, wherein the bioindicator is a cell suspension of a bacterium that is sensitive to an antimicrobial.

13. The apparatus of claim 11, wherein the bioindicator tube comprises a top portion that is fitted with a microfilter cartridge for separating microbial cells from dispensed liquid.

14. The apparatus of claim 9 further comprising a cooling system arranged to control the temperature of the fraction collector unit.

15. The apparatus of claim 14, wherein:
the cooling system comprises a refrigerated compartment exterior to the reactor vessel; and
the fraction collector unit is contained within the refrigerated compartment.

16. The apparatus of claim 14, wherein the cooling system comprises a Peltier device.

* * * * *